(12) United States Patent
Wu et al.

(10) Patent No.: US 9,689,670 B2
(45) Date of Patent: Jun. 27, 2017

(54) THICKNESS AND CONVEXITY DETECTION DEVICE FOR PLATE STRIP

(75) Inventors: Zhifang Wu, Beijing (CN); Jigang An, Beijing (CN); Yuai Zhang, Beijing (CN); Jichen Miao, Beijing (CN); Litao Li, Beijing (CN); Guilai Xing, Beijing (CN); Liqiang Wang, Beijing (CN); Zhentao Wang, Beijing (CN); Ximing Liu, Beijing (CN); Jian Zheng, Beijing (CN); Yibin Huang, Beijing (CN); Xiaojing Guo, Beijing (CN); Chunming Tan, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 922 days.

(21) Appl. No.: 14/009,123

(22) PCT Filed: Mar. 29, 2012

(86) PCT No.: PCT/CN2012/073227
§ 371 (c)(1),
(2), (4) Date: Aug. 4, 2014

(87) PCT Pub. No.: WO2012/136114
PCT Pub. Date: Oct. 11, 2012

(65) Prior Publication Data
US 2015/0226549 A1  Aug. 13, 2015

(30) Foreign Application Priority Data
Apr. 2, 2011  (CN) .......................... 2011 1 0084366

(51) Int. Cl.
*G01B 15/04* (2006.01)
*G01B 15/02* (2006.01)
*G01N 33/20* (2006.01)

(52) U.S. Cl.
CPC ............. *G01B 15/02* (2013.01); *G01B 15/04* (2013.01); *G01N 33/20* (2013.01)

(58) Field of Classification Search
CPC ...................................................... G01B 15/04
(Continued)

(56) References Cited

U.S. PATENT DOCUMENTS 3,655,979 A * 4/1972 Jernigan, Jr. .......... G01N 23/16
250/360.1
2007/0280415 A1* 12/2007 Waterson ................ B21B 38/02
378/55

FOREIGN PATENT DOCUMENTS

CN    1936498 A    3/2007
CN    1958184 A    5/2007
(Continued)

OTHER PUBLICATIONS

Wang Kai,Wu Hai-feng,Zheng Jian,Peng Shuai-jun(Institute of Nuclear and New Energy Technology,Tsinghua University,Beijing 100084,China); Research on Numbers of Radiation Sources in Strip Crown Measurement; Nuclear Electronics & Detection Technology Feb. 2009; Mar. 2009, vol. 29, No. 2, pp. 474-476.

*Primary Examiner* — Bryan Bui
(74) *Attorney, Agent, or Firm* — AKC Patents LLC; Aliki K. Collins

(57) ABSTRACT

The invention relates to a device for detecting the thickness and crown of plates and strips, belonging to the field of nuclear technology applications. The device comprises a C-frame; two ray source mounted in an upper arm of the C-frame and distributed at an interval along the width direction of a steel plate/strip; two rows of gas-pressurized ionization chamber detector arrays mounted in a lower arm of the C-frame and distributed at an interval along the moving direction of the plate/strip; collimators mounted below the two ray source, the collimators enabling the rays (Continued)

of each ray source to only irradiate to a corresponding row of detectors; pre-amplifier modules connected with the detector arrays; a data collector connected with the pre-amplifier modules; a data processing and displaying computer connected with the data collector; and a cooling water and pressurized air service system and a control system for ensuring system operation and monitoring. The device of the invention is simple in structure and high in dynamic measurement accuracy, and the detectors have the advantages of small temperature drift, irradiation resistance, high spatial resolution, high cost performance and the like.

3 Claims, 2 Drawing Sheets

(58) Field of Classification Search
USPC .......................................................... 702/167
See application file for complete search history.

(56) References Cited

FOREIGN PATENT DOCUMENTS

| CN | 1962102 A | 5/2007 |
|---|---|---|
| CN | 2928283 Y | 8/2007 |
| CN | 201455009 U | 5/2010 |
| CN | 102200434 B | 9/2011 |
| CN | 202092619 U | 12/2011 |
| GB | 2138561 A | 10/1984 |

* cited by examiner

THICKNESS AND CONVEXITY DETECTION DEVICE FOR PLATE STRIP

FIELD OF THE INVENTION

The present invention belongs to the field of nuclear technology applications, in particular to a device for detecting the thickness, crown, shape and the like of plates and strips on an industrial hot rolling or cold rolling production line.

BACKGROUND OF THE INVENTION

A crown gauge is key equipment for production and control of plates and strips, and plays an important role in improving the yield and quality of plates and strips. As the rolling temperature of hot rolled steel plate/strips is high (over 800° C.), and there are dust, water vapor and the like in the environment, non-contact ray-type measuring methods have great advantages. The performance of the detector of a ray-based crown gauge is one of the key factors determining the measurement accuracy and the detection speed of the crown gauge. Some of the existing crown gauges adopt a single row of solid detectors (as described in the product documents of Thermo Scientific), and in spite of the advantages of high response speed, small size and light weight, also have some shortcomings.

Firstly, the afterglow is long; a photodiode is not irradiation-resistant and has a short service life; the requirement on the working environment temperature is high; and thermostatic control of the working environment is required.

Secondly, as different ray sources share a single row of detectors, a rotating shutter is needed so that two ray sources emit X-ray alternately, and thus the mechanical structure is complicated, and vibration interference occurs.

Thirdly, as rays of two ray sources are measured successively by the same row of detectors, the distance between detected positions of the two ray sources on a steel plate/strip is related to the operating speed of the steel plate/strip, and as thickness reconstruction of the steel plate/strip is obtained by using measured data of the two ray sources, the measurement accuracy is reduced when the operating speed of the steel plate/strip is high.

In addition, a gas ionization chamber detector is adopted in some cases (as described in product documents of IMS Messysteme GmbH), but the ionization chamber used in these cases is large in size, an thus the resolution cannot meet the requirement of steel plants and needs to be increased by oscillating of a C-frame along the width direction of the steel plate/strip. This aspect results in complicated mechanical and control systems; and meanwhile, as the weight of the C-frame is heavy, the swinging frequency should not be too high, generally being 1.5 Hz to 2 Hz, such that when the steel plate/strip moves, data for calculating the thickness on the same cross section are obtained from two different cross sections (with a distance of several to tens of meters), thereby reducing the dynamic performance of the gauge. In the aspect of ray sources, as the field angle of the adopted ray sources is small, and cannot cover the width of the steel plate/strip, a projection needs two ray sources in the width direction of the steel plate/strip, and if ray sources for obtaining another projection are added, four ray sources would be needed in total, so the structure is complicated.

SUMMARY OF THE INVENTION

The object of the present invention is to overcome the defects of the existing ray-based crown detecting technologies, and provide a novel device for detecting the thickness and crown of plates and strips, which can conveniently obtain two ray projections on a cross section of a plate/strip simultaneously, thereby detecting the thickness, the crown and the profile of the plate/strip, and which only adopts two ray sources, two rows of gas ionization chamber arrays and information processing systems. Compared with a single row of solid detectors adopted in a system, the detectors have the advantages of small temperature drift, irradiation resistance, good stability, high cost performance and the like, and has a simple mechanical structure; meanwhile, compared with the existing device adopting an ionization chamber, the novel device has high resolution, good dynamic performance, a reduced number of ray sources and a simple mechanical structure.

The device for detecting the thickness and crown of plates and strips provided by the present invention is characterized by comprising a C-frame; two ray sources mounted in an upper arm of the C-frame and distributed at an interval along the width direction of the steel plate/strip; two rows of gas-pressurized ionization chamber detector arrays mounted in a lower arm of the C-frame and distributed at intervals along the moving direction of a plate/strip; collimators mounted below the two ray sources, the collimators enabling the rays of each ray source to be only irradiated to one corresponding row of detectors; pre-amplifier modules connected with the detector arrays; a data collector connected with the pre-amplifier module; a data processing and displaying computer connected with the data collector; and a cooling water and pressurized air service system and a control system for ensuring system operation and monitoring.

The device has the following characteristics and beneficial effects:

Gas-pressurized ionization chambers are adopted as the detectors in the present invention, and compared with solid detectors adopting "CsI scintillators and photodiodes", the detectors are less affected by the temperature, are small in temperature drift and do not need thermostatic control like in the case of the solid detectors. Meanwhile, the detectors have the advantages of irradiation resistance, small leak current, long service life, high reliability, auto-collimation, low cost and the like compared with the solid detectors.

Compared with those adopting the arrangement of a single row of solid detector arrays, the device adopting the arrangement of two rows of gas ionization chamber arrays has the effects that on the one hand, a high-speed operating rotating shutter necessary for time-division use of the single row of detectors by the two ray sources is omitted, thus simplifying the mechanical structure and increasing the system reliability; and on the other hand, it also ensures that the two rows of detector arrays can obtain data simultaneously, thereby improving the dynamic measurement accuracy of the system. Compared with a system adopting four ray sources and four rows of gas ionization chamber detectors, the device uses two less ray sources and adopts the gas-pressurized ionization chamber detectors with a volume smaller than that of the ionization chamber detectors, can meet the requirement on spatial resolution without wiggling the C-frame along the width direction of the steel plate/strip like in the existing system of IMS, thus greatly simplifying the complexity of mechanical and control systems, and improving the dynamic detection performance of the system.

DETAILED DESCRIPTION OF THE EMBODIMENTS

The specific content of the present invention will be described below in details in conjunction with the accompanying drawings.

Figure 1:
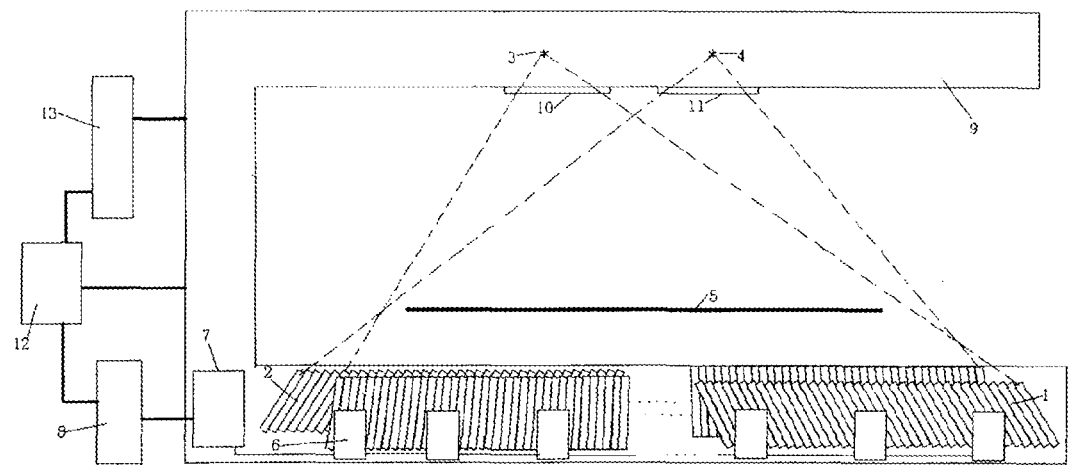
FIG. 1 is a front schematic view of a device for detecting the thickness and crown of plates and strips according to the present invention.

A device for detecting the thickness and crown of plates and strips provided by the invention, as shown in FIG. 1, comprises a C-frame 9; two ray sources 3 and 4 mounted in an upper arm of the C-frame and distributed at an interval along the width direction of a steel plate/strip; two rows of gas-pressurized ionization chamber detector arrays 1 and 2 mounted in a lower arm of the C-frame and distributed at an interval along the moving direction of the plate/strip; collimators 10 and 11 mounted below the two ray sources, the collimators enabling rays of each ray source to only irradiate to a corresponding row of detectors; pre-amplifier modules 6 connected with the detector arrays; a data collector 7 connected with the pre-amplifier modules; a data processing and displaying computer 8 connected with the data collector; and a control system 12 and a cooling water and pressurized air service system 13 for ensuring system operation and monitoring, connected with the computer 8 and the crown gauge C-frame 9 respectively.

Figure 2:
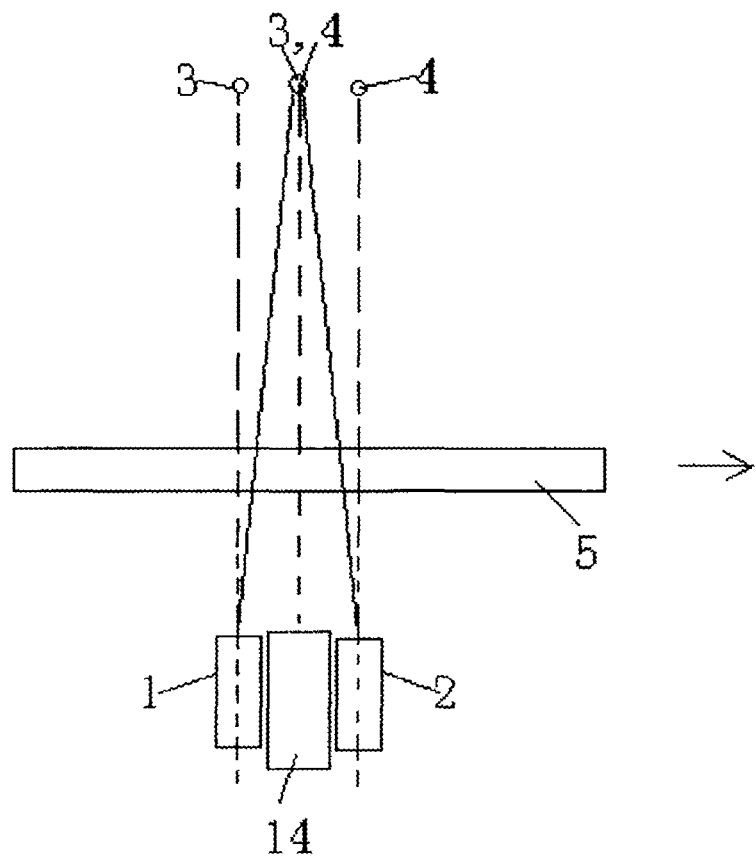
FIG. 2 is a thickness measurement schematic diagram of the device for detecting the thickness and crown of plates and strips according to the present invention.

The positional relation between the detector arrays 1 and 2 in the width direction of the steel plate/strip 5 is as shown in FIG. 2. The two ray sources 3 and 4 can be right above the two rows of detector arrays 1 and 2 respectively, and can also be right above the central lines of the two rows of detector arrays 1 and 2. The device also comprises a support seat 14 for fixing the two rows of detector arrays, and the two rows of detector arrays are symmetrically distributed at both sides of the support seat 14. As the central distance between the detector array 1 and the detector array 2 is very short (4.6 cm in the embodiment, converted to about 3.6 cm on the steel plate/strip), and the thickness of the steel plate/strip can be considered consistent within this range, so it can be approximately considered that the same cross section of the steel plate/strip is detected by the two rows of detector arrays.

The specific implementing ways and functions of the component parts are described below respectively:

The detector arrays 1 and 2 are respectively composed of hundreds of small-size centripetally arranged gas-pressurized ionization chambers (a product with proprietary intellectual property right of the applicant, already applied for invention patent entitled "gas-ionization middle & low energy X-ray and γ-ray detector") (the gas-pressurized ionization chambers used in the embodiment are 10×20×100 mm in width-length-height dimensions), and have the advantages of small temperature drift, irradiation resistance, high spatial resolution, high cost performance and the like. The specific number of the ionization chambers is determined by the width of the steel plate/strip 5 under detection, and in order to ensure resolution, the size of the detector arrays in the width direction of the steel plate/strip is generally smaller than 20 mm; in this case, the detector array 1 is corresponding to the ray source 3, and the ray window of each ionization chamber in the detector array 1 faces toward the ray source 3; and the detector array 2 is corresponding to the ray source 4, and the ray window of each ionization chamber in the detector array 2 faces toward the ray source 4. The ray sources 3 and 4 can be ray sources, and can also be radioisotope sources. In the embodiment, 225 KV X-ray sources of COMET is adopted.

Figure 3:
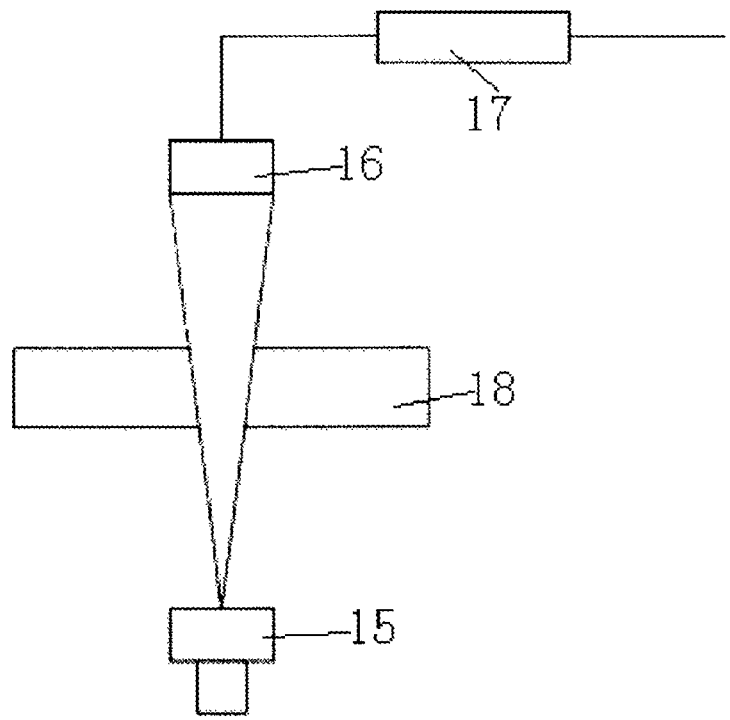
FIG. 3 is a side schematic view of the device for detecting the thickness and crown of plates and strips according to the present invention.

Now the principle of obtaining a thickness signal by the detector is described in conjunction with FIG. 3. After X-rays emitted by the ray source 15 pass through an object under detection 18, the intensity thereof will be attenuated somewhat and follows the following formula:

$$I_m = I_0 \cdot e^{-\mu h} \quad (1)$$

In the formula, $I_0$ represents the intensity of the ray before they pass through the object under detection 18; $I_m$ represents the intensity of the ray after they pass through the object under detection 18; $\mu$ represents the linear absorption coefficient of the object under detection for the X-ray; and h represents the thickness of the object under detection 18.

$\mu$ is related to the components of the object under detection 18 and the energy of the ray. The composition of the object under detection 18 is complicated, and the X-ray have a very wide energy spectrum, so in practical applications, the relation between $I_m$ and h given in formula (1) cannot be relied on, and it needs to measure $I_0$ through an experiment and determine a relation curve between h and $I_m$, and this process is also called calibration. A detector 16 converts a detected irradiation intensity signal $I_m$ to a current signal in proportion thereto, which is amplified though a signal processor 17. The thickness h of the object under detection can be known from an amplified detector output signal and the relation curve between h and $I_m$. The pre-amplifiers 6 amplify weak current signals output by the ionization chambers in the detector arrays 1 and 2, and in the embodiment signal amplification circuits of every 16 ionization chambers are integrated in one pre-amplifier module. The amplifiers adopt high-gain low-noise electronic components.

In the embodiment the data collector 7 is composed of a conventional current input A/D converter, a CPLD (Complex Programmable Logic Device) and a SCM (Single Chip Microcomputer). Hundreds of ionization chamber signals of the two rows of detector arrays amplified by the pre-amplifiers 6 are collected, and the collected data are quickly transmitted to the data processing and displaying computer 8. In the embodiment, data of all the detectors are collected and transmitted every 10 ms.

The data processing and displaying computer 8 is used for storing calibration curves, scatter correction data, and alloy compensation and temperature compensation coefficients, reading data transmitted from the data collector 7, reconstructing the cross section thickness of the steel plate/strip, and calculating and displaying parameters of crown and the like. The data processing and displaying computer in the embodiment can be a conventional industrial PC with a network card. All the above calibration curves are stored in the data processing and displaying computer 8. In every 10 ms, the data processing and displaying computer 8 receives the data of the two rows of detector arrays sent by the data collector 7. Then measured values of the detectors are subjected to certain scatter correction to obtain $I_m$, then table look-up is performed with the relation curve between h and $I_m$ to obtain the thickness h of the steel plate/strip. For each detector, a thickness can be obtained, and for a row of detector arrays, a thickness projection of the cross section of the steel plate/strip can be obtained. From the data of the two rows of detector arrays, two projections of the cross section of the steel plate/strip can be obtained. The transverse thickness distribution of the plate/strip can be calculated by a certain reconstruction algorithm according to the two projections and geometrical configuration parameters, and crown data can be obtained in real time according to the thickness distribution.

Figure 4:
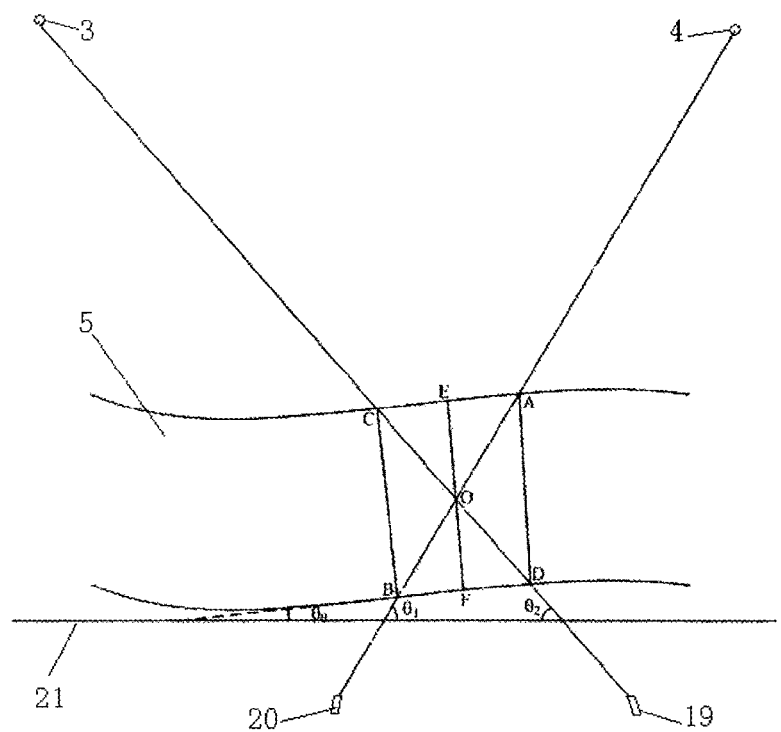
FIG. 4 is an algorithm schematic diagram of the device for detecting the thickness and crown of plates and strips according to the present invention.

The basic principle of the reconstruction algorithm is introduced below in conjunction with FIG. 4. 19 represents a detector unit in the detector array 1 corresponding to the ray source 3; 20 represents a detector unit in the detector array 2 corresponding to the ray source 4; and 21 represents the surface of a roller bed (equipment for conveying a rolled steel plate/strip on a steel plate/strip rolling production line, with the steel plate/strip to be detected by the measurement device located thereon) As shown in FIG. 4, certain included angles (such as $\theta_1$ and $\theta_2$, the angle values are given and input into the computer in advance) are formed respectively between the detector units 19 and 20 and the corresponding ray sources 3 and 4; and for the lengths of AB and CD in the figure, data measured by the detector unit 19 of the detector array 1 and the detector unit 20 of the detector array 2 respectively are subjected to scatter correction, and then reversely looked up in respective relation curves between h and $I_m$ to obtain thicknesses $h_1$ and $h_2$ and then obtain the lengths of AB and CD according to geometrical relation.

$$AB = h_1/\sin\theta_1 \quad (2)$$

$$CD = h_2/\sin\theta_2 \quad (3)$$

Then the thickness EF at the point O and the inclination angle $\theta_0$ of the steel plate/strip can be represented by $\theta_1$, $\theta_2$, $h_1$ and $h_2$.

Within a very small range, it can be considered that AC and BD are both straight lines and are parallel to each other; EF is the thickness of the point O and is perpendicular to AC and BD. It can be seen from the geometrical relations that:

$$\angle ABD = \theta_1 - \theta_0 \quad (4)$$

$$\angle CDB = \theta_2 + \theta_0 \quad (5)$$

According to the definition of a trigonometric function, it follows that:

$$EF = AB \cdot \sin(\theta_1 - \theta_0) \quad (6)$$

$$EF = CD \cdot \sin(\theta_2 + \theta_0) \quad (7)$$

EF is eliminated, and it is set that $AB/CD = h_1 \sin\theta_2/(h_2 \sin\theta_1) = n$, then:

$$\frac{\sin(\theta_2 + \theta_0)}{\sin(\theta_1 - \theta_0)} = n \quad (8)$$

The trigonometric function is expanded and reorganized, and we can obtain:

$$\tan\theta_0 = \frac{n\sin\theta_1 - \sin\theta_2}{n\cos\theta_1 + \cos\theta_2} \quad (9)$$

Thus we obtain the inclination angle $\theta_0$, which is then substituted into the expression of EF to obtain the thickness EF.

In the above algorithm, AB and CD are auxiliary lines for the algorithm, and both the calculated EF and angle θ are only related to $\theta_1$, $\theta_2$, $h_1$ and $h_2$. The target centers of the ray sources can be or not be right above the detector arrays, as shown in FIG. 2. The algorithm is applicable to both cases. When the target center of the ray source 3 is right above the detector array 1, and the target center of the ray source 4 is right above the detector array 2, AB and CD are paths through which the rays actually pass. Otherwise, when the detector arrays are not right below the ray sources, AB and CD are only auxiliary lines of the algorithm. However, from the perspective of improving the detecting efficiency of the detectors, it is better for the target centers of the ray sources to be right above the detector arrays.

The C-frame 9 is used for placing the detection equipment, and the width thereof is determined by the width of the steel plate/strip that can be detected, and the designed height thereof is determined by factors such as the ray coverage angle and the like. In this embodiment, it can be formed by welding a stainless steel with a certain thickness, and the upper and lower arms can be connected through bolts to facilitate assembly and disassembly. Water jackets are welded on the lower surface of the upper arm and the upper part of the lower arm, and circulating cooling water is introduced into the water jackets.

The collimators 10 and 11 are used for collimating ray to narrow sheet-like sector beams, and can be made of a metal, such as lead, tungsten and the like, or an alloy thereof.

The control system 12 is used for monitoring the operation state of the system, transmitting control commands, and coordinating the subsystems to operate normally. In this embodiment, it is composed of a conventional touch screen and a PLC (Programmable Logic Controller). The cooling water and pressurized air service system 13 supplies cooling circulating water to the water jackets of the C-frame 9 and the ray sources 3 and 4, introduces dry air to the lower arm to ensure the ambient humidity required for normal working of the detectors, and can be manufactured by conventional technologies.

Now the measurement process is described in conjunction with FIG. 1. When the rolled steel plate/strip 5 passes through a passage defined by the C-frame 9 of the crown gauge, and the control system 12 detects that the steel plate/strip reaches the two ray irradiation areas, the two ray sources emit rays. The rays emitted by the ray source 3 are collimated to a narrow sheet-like sector beam by the collimator 10 mounted below, and then irradiate to the steel plate/strip 5 from the perspective shown in FIG. 1, and the rays, after penetrating the steel plate/strip 5, pass through a rear collimator (for removing scattered rays) and enter the aligned detector array 1, and signals of the detector array 1 are amplified by the pre-amplifiers 6. Similarly, the detector array 2 detects attenuated signals emitted by the ray source 4 after passing through the steel plate/strip, and the attenuated signals are amplified by the pre-amplifiers 6. The data collector 7 collects signals of the two rows of detector arrays 1 and 2 amplified by the pre-amplifiers at regular time intervals, and transmits the measured data to the data processing and displaying computer 8, and the data processing and displaying computer 8 calculates the inclination angles $\theta_0$ and the thicknesses EF of the points on the cross section according to the above measurement principle, automatically performs further correction on the thickness values, such as alloy compensation, temperature compensation and the like, and finally calculates to give the true thickness at each point on the cross section, and a crown value can be further obtained according to formula (10):

$$C = e - \frac{1}{2}(e_1 + e_2) \qquad (10)$$

In the formula, e represents the thickness at the center of the steel strip; and $e_1$ and $e_2$ represent the thicknesses at both ends of the steel strip.

In the embodiment, the data collector obtains the measured data every 10 ms, and the data acquisition time interval can be adjusted to be higher or lower according to the requirement of a plant.

The outstanding characteristic of the present invention lies in that two ray sources and two rows of gas-pressurized detectors are used to implement measurement on the parameters such as the thickness of the cross section, the crown and the like of the steel plate/strip.

Compared with the system adopting two sources and a single row of detectors (such as products of Thermo Scientific), the device of the invention avoids the use of a high-speed operating rotating shutter which is necessary for time-division use of the single row of detectors by the two ray sources, and have a simplified mechanical structure and improved system reliability; in addition, the two rows of detector arrays can acquire data simultaneously, and the distance on the steel plate/strip corresponding to the two groups of data is fixed and very short (3.6 cm in this embodiment), thus avoiding the phenomenon that when a single row of detectors acquire data in a time-division manner, the distance on the steel plate/strip corresponding to the two groups of data changes with the operation speed of the steel plate/strip (if the operation speed of the steel plate/strip is 20 m/s, and a group of data are measured for each source in every 5 ms, then the distance is 10 cm), and improving the measurement accuracy; moreover, compared with solid detectors, the gas ionization chamber detectors have the advantages of small temperature drift, irradiation resistance, high cost performance and the like.

Compared with a system adopting four ray sources and four rows of gas ionization chamber detectors (such as products of IMS), the device uses two less ray sources and adopts the gas-pressurized ionization chamber detectors with proprietary intellectual property right, having a volume (10×20×100 mm in width-length-height dimensions in this embodiment) smaller than that of the ionization chamber detectors, can meet the requirement on spatial resolution without wiggling the C-frame along the width direction of the existing steel plate/strip like in the system of IMS, thus greatly simplifying the complexity of the mechanical and control systems; meanwhile, as the wiggling frequency of the C-frame is not high, being generally about 1.5 times per second, data of a projection obtained by the measurement device requiring wiggling the C-frame is composed of two parts, and the distance between the two positions on the steel plate/strip corresponding to the two parts of data may be large (for example, if the operation speed of the steel strip is 20 m/s, then the distance is not smaller than 13 m), this can result in poor dynamic performance of the system, and thus the device of the invention has improved dynamic performance of the system compared therewith.

The invention claimed is:

1. A device for detecting the thickness and crown of plates and strips, comprising:
 a C-frame;
 two ray sources mounted in the upper arm of C-frame and distributed at an interval along the width direction of a steel plate/strip;
 two rows of gas-pressurized ionization chamber detector arrays mounted in the lower arm of C-frame and distributed at an interval along the moving direction of the plate/strip;
 collimators mounted below the two ray sources, the collimators enabling ray of each source to only irradiate to a corresponding row of detectors;
 pre-amplifier modules connected with the detector arrays;
 a data collector connected with the pre-amplifier modules;
 a data processing and image displaying computer connected with the data collector; and
 a cooling water and pressurized air service system and a control system for ensuring system operation and monitoring;
 wherein each of the two rows of detector arrays are corresponding to a ray source, and the two rows of detector arrays are symmetrically fixed on the both sides of a support seat;
 wherein each row of detector arrays are composed of hundreds of gas-pressurized ionization chamber units which are centripetally arranged with the target of the corresponding ray source as the circle center, the detector arrays being in linear arrangement, and the dimension of each gas-pressurized ionization chamber unit meets the requirement of spatial resolution of the plate/strip;
 wherein the dimension of the gas-pressurized ionization chamber units in the width direction of the plate/strip to be detected is smaller than 20 mm;
 wherein the rays emitted by the two ray source are respectively collimated to narrow sheet-like sector beams by the collimators mounted below and irradiate to the plate/strip to be detected, and the rays, after penetrating the steel plate/strip to be detected, pass through a rear collimator for removing scattered rays and enter the corresponding detector array, and signals generated by the detector arrays are amplified by the pre-amplifier modules connected therewith;
 wherein the data collector collects the signals of the two rows of detector arrays amplified by the pre-amplifier modules at regular time intervals, and transmits the measured data to the data processing and image displaying computer;
 wherein the data processing and image displaying computer calculates the inclination angles and the thicknesses of points on the cross section, and finally calculates the true thickness at each point on the cross section, and obtains a crown value C of the plate/strip to be detected according to the following formula:

$$C = e - \frac{1}{2}(e_1 + e_2)$$

in the formula, e represents the thickness at the center of the plate/strip to be detected;
and $e_1$ and $e_2$ represent respectively the thicknesses at both ends of the plate/strip.

2. The detection device according to claim 1, characterized in that the used ray source are any of X-ray source and isotope γ-ray source, and the field angle of each ray source covers the width of the whole plate/strip.

3. The detection device according to claim 1, characterized in that the plate/strip to be detected is a plate/strip on an industrial hot rolling or cold rolling production line.

* * * * *